United States Patent [19]
Zander

[11] Patent Number: 4,968,486
[45] Date of Patent: Nov. 6, 1990

[54] DEVICE FOR ABSORBING SHOCK TO A CONTAINER

[75] Inventor: Dennis R. Zander, Penfield, N.Y.

[73] Assignee: Eastman Kodak Company, Rochester, N.Y.

[21] Appl. No.: 380,843

[22] Filed: Jul. 14, 1989

[51] Int. Cl.[5] .......... B01L 3/00; B65D 81/02; G01N 21/00; C12M 1/16

[52] U.S. Cl. .......... 422/102; 422/58; 206/521; 206/521.8; 435/299; 435/301

[58] Field of Search .......... 422/102, 56, 57, 58; 220/66, 70; 215/1 C; 206/521, 521.8; 435/296, 299, 300, 301

[56] References Cited

U.S. PATENT DOCUMENTS

| | | | |
|---|---|---|---|
| 3,190,731 | 6/1965 | Weiskoff . | |
| 3,481,712 | 12/1969 | Bernstein et al. . | |
| 3,627,432 | 12/1971 | Bergmann . | |
| 3,680,967 | 8/1972 | Engelhardt . | |
| 3,713,985 | 1/1973 | Astle | 435/301 |
| 3,754,872 | 8/1973 | Zauft . | |
| 4,021,124 | 5/1977 | Sarstedt . | |
| 4,094,641 | 6/1978 | Friswell . | |
| 4,106,907 | 8/1978 | Charlton et al. . | |
| 4,234,316 | 11/1980 | Hevey . | |
| 4,318,986 | 3/1982 | Richardson et al. | 435/299 |
| 4,358,028 | 11/1982 | Chiquiar-Arias . | |
| 4,473,530 | 9/1984 | Villa-Real | 422/58 |
| 4,639,419 | 1/1987 | Olson et al. . | |
| 4,673,639 | 6/1987 | Slifkin . | |
| 4,735,904 | 4/1988 | Starr | 436/74 |

FOREIGN PATENT DOCUMENTS

| | | |
|---|---|---|
| 82/00980 | 7/1982 | PCT Int'l Appl. . |
| 83/01070 | 7/1983 | PCT Int'l Appl. . |

OTHER PUBLICATIONS

*Machine Design*, Materials Reference Issue, Apr. 16, 1987, pp. 153 and 160.

*Primary Examiner*—Robert J. Warden
*Assistant Examiner*—Thalia P. Vassilatos
*Attorney, Agent, or Firm*—Dana M. Schmidt

[57] ABSTRACT

There is described a container having a closed end and a reagent deposited in the closed end. The container is provided with means for preventing shock from being transmitted to the closed end when that end strikes a hard object.

6 Claims, 1 Drawing Sheet

DEVICE FOR ABSORBING SHOCK TO A CONTAINER

FIELD OF THE INVENTION

This invention relates to a container having reagents deposited in a closed end and means for preventing the dislodging of the reagents.

BACKGROUND OF THE INVENTION

Examples of the state of the art of placing dried reagents in the closed end of a container are found in U.S. Pat. No. 4,639,419 entitled "Immunological Color Change Test Involving Two differently Colored Reagent Spots" issued on Jan. 27, 1987 and U.S. Pat. No. 4,673,639 entitled "Dry Form Micronitrous Acid Streptococci Extraction-Agglutination Test" issued on Jun. 16, 1987. To date, these containers have been less than completely satisfactory since their construction has ignored the fact that if the closed end strikes an object, the reagent can be dislodged. Furthermore, even if the dislodging problem is acknowledged, it is not sufficient as the solution to the problem, to simply construct the bottom portions of the container to be much thicker, since at least the side wall portion adjacent the bottom wall of the contaner must be sufficiently flexible as to allow the container to be squeezed right above the bottom wall. Such squeezing is used to redissolve the stored reagents more rapidly.

There has been a need, therefore, prior to this invention, for an improved container with a means for preventing dislodging of the reagent when the closed end strikes an object, without interfering with the flexibility of the container.

SUMMARY OF THE INVENTION

I have constructed a container that solves the aforesaid problems concerning the use of a container which has deposits of reagents in its closed end.

More specifically, in accord with one aspect of the invention, there is provided a container having a sidewall, a bottom wall joined to the sidewall at a junction point, and a reagent deposited on an inside surface of the bottom wall, at least a portion of the sidewall adjacent the bottom wall being flexible.

the improvement wherein the container further includes absorber means extending from the bottom wall at or below the junction point for absorbing shock, the absorber means having a length and thickness sufficient, when the container is dropped bottom wall first a distance of 68.6 cm onto a hard surface with a container weight of 1.716 g, to prevent a dried reagent weighing 0.016 g deposited onto the inside surface from being dislodged.

Thus, it is an advantageous feature of the invention that a container is provided which includes an absorber means preventing subsequent dislodging of deposited reagents located in the said closed end.

It is a related advantageous feature of the invention that such absorber means are provided without significantly interfering with the squeezability of the container.

Other advantageous features will become apparent upon reference to the following Desription of the Preferred Embodiments, when read in light of the attached drawings.

DESCRIPTION OF THE PREFERRED EMBODIMENTS

The invention is described hereinafter in connection with certain preferred embodiments wherein the container is particularly suited for absorption of shock at its closed end through use of a reinforcing means extending from said closed end. Thus, plastic is the preferred construction. Glass is also useful, if the absorbing means can be suitably attached.

The terms "above", "below" and the like refer to orientations of parts when the device is in its preferred orientation for use, that is, when the container is generally vertical with its open end up.

Figure 1:
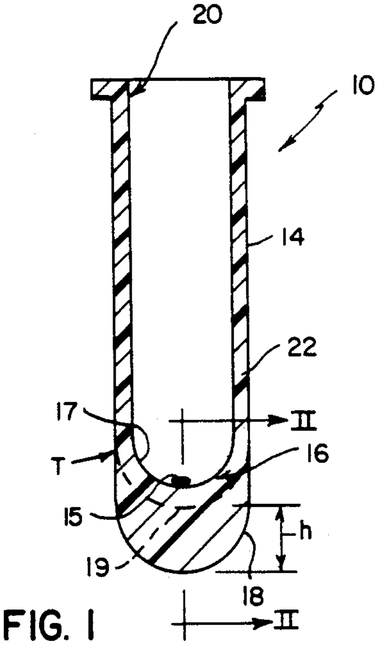
FIG. 1 is an elevation view in section of a container constructed in accordance with the invention.

As discussed hereinafter, the preferred embodiment illustrated in FIG. 1 is a container 10 having a side wall 14 that is preferably cylindrical, a closed end provided by a bottom wall 16 joined to side wall 14 at junction T, FIG. 1, and at least one reagent 15 deposited on inside surface 17 of bottom wall 16. Preferably, opposite end 20 is an open end of conventional construction that can be stoppered. At least portions 22 of side wall 14, that is, the portion adjacent to junction T, are flexible, to allow container 10 to be squeezed. This encourages the redissolving of reagent 15 when water or sample is added. Reagent(s) 15 can be present for any purpose including extraction of chlamydial, gonococcal or herpes antigen as disclosed in commonly owned U.S. Ser. No. 381,219 filed on even date herewith by Hinckley, et al and entitled "Extracting Device for Extracting Antigens", wherein the preferred reagents for depositing and drying in the extraction container are dithiothreitol, a reducing agent, with polyacralamide, a stabilizer and TRISMA (tris-hydroxyaminomethane).

Also, in U.S. Ser. No. 255,928, commonly owned and filed on Oct. 7, 1988 by Pronovost, et al and entitled "High pH Extraction Composition And Its Use To Determine A Chlamydial Gonococcal or Herpes Antigen" a composition is disclosed which is useful for extracting antigen from chlamydial, gonococcal or herpes organisms having a pH of at least about 8 and comprising a strong base and an alcoholamine. Other addenda preferably included in the extraction composition include a cationic surfactant, one or more reducing agents, preservatives to prevent hydrogen peroxide activity and chelating agents. It is conceivable that either the strong base, the alcoholamine, the cationic surfactant or the reducing agent could be used for the same purpose.

Examples of other reagents which could be used for other purposes in this invention are enzymes, enzyme substrates, antibodies, antigens, haptens, inorganic and organic reagents, buffers, salts and the like, as well as radioactively tagged or fluorescent reagents of the foregoing types including nonisotopic tage such as enzymes, cofactors, luminescent agents and the like as disclosed in U.S. Pat. No. 4,234,316 entitled "Device for Delivering Measured Quantities of Reagents into Assay Medium" issued on Nov. 18, 1980.

In further accord woith the invention, the container is improved by absorber means 18, FIG. 1, which extend from bottom wall 16 at or below junction T. This location of the absorber means is considered critical, since locating it above the junction tends to interfere with the flexibility of portions 22 of side wall 14. The reinforcing means 18 preferably comprise a flexible flange extending from the surface 19 of wall means 14 approximately at the middle of bottom wall 16, FIG. 3. It can be constructed by molding flexible material consistent or compatible with that used in the construction of the wall means, 14, FIG. 1, onto the closed end. The height "h", FIG. 1, and the thickness "t", FIG. 2, of flange 18 need to be controlled as described hereinafter, to provide effective shock resistance.

Although flange 18 is shown curved, it can also have right-angle corners, not shown.

Figure 3:
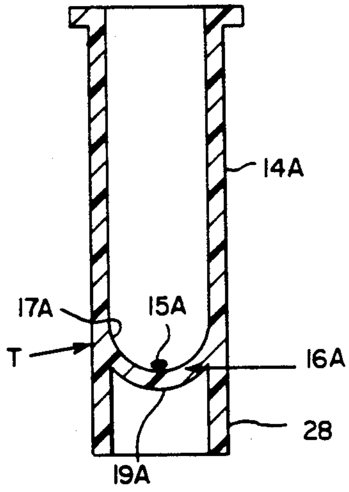
FIG. 3 is a elevation view in section similar to FIG. 1 but illustrating a separate embodiment.
Figure 4:
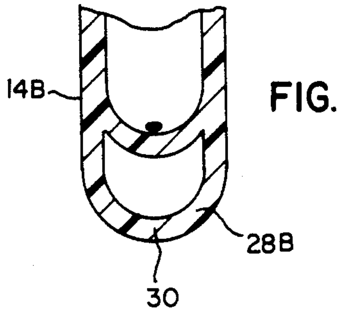
FIGS. 4–6 are fragmentary section views similar to that of FIG. 1 or 3, but illustrating alternate embodiments.
Figure 5:
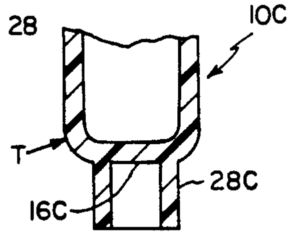

Alternate embodiments are illustrated in FIGS. 3-5. Parts similar to those previously described bear the same reference numeral to which the distinguishing suffix "A", "B" or "C" is appended. Thus, the container similarly comprises side wall 14A joined to bottom wall 16A at junction T and at least one reagent 15A deposited inside of bottom wall 16A. However, the absorbing means which extends from bottom wall 16A, is a flexible skirt 28 extending downward from surface 19A, opposite to inside surface 17A. This skirt can be constructed with a variety of shapes. As shown, it preferably extends around the circumference of closed end 16A. In FIG. 4, the skirt joins itself to form a shock-absorbing bubble 28B. (This can be fabricated by joining skirt portions together at junction 30.) In FIG. 5, skirt 28C is joined to wall 16C below junction T.

Variations of these embodiments could include one or more thin, flexible prongs (not shown) extending from the closed end of the tube.

Figure 6:
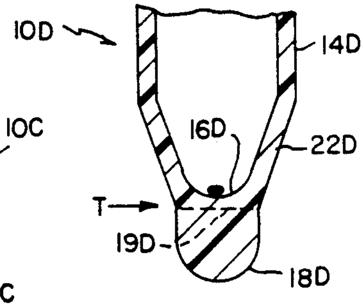

The sidewall of the container can have a compound shape, as illustrated in FIG. 6. Parts similar to those previously described bear the same reference numeral, to which the distinguishing suffix "D" has been appended. Thus, container 10D has a sidewall 14D joined to a bottom wall 16D at junction T, and an absorber flange 18D projecting from outside surface 19D. However, sidewall 14D has a portion 22D, which preferably is the squeezable flexible portion, that is conically shaped rather than cylindrically shaped like the rest of side wall 14D.

Figure 2:
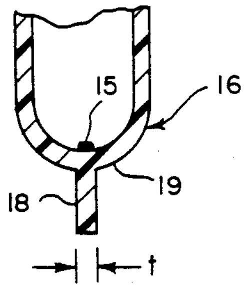
FIG. 2 is a fragmentary section view taken generally along the line II—II of FIG. 1.

To demonstrate the effect that the height and thickness of the absorber means have, on its function, the design of FIGS. 1 and 2 was tested as follows. (Similar constraints apply to the skirt or bubble configurations shown, albeit different values may apply.)

EXAMPLE 1

In this example, a set of 100 identical polyethylene tubes, 7.57 cm long from the top of the open end 20 to the bottom of the absorber means 18, FIG. 1, was dropped at a height of 68.6 cm from a solid flooring. (The 68.6 cm is measured from the bottom of the absorber means, and is equivalent to 30 inches measured from the top open end.) The flange 18 was 2.54 mm (0.1 inch) long and 1.0 mm thick, and the sidewall 14 had a thickness of about 0.5 mm. Each tube had a dried reagent deposit as shown in FIG. 1, weighing about 0.016 g, with a total tube weight of about 1.7 g. The set of tubes was dropped 5 separate times, and the cumulative number of times there was a tube that failed, i.e., caused dislodging of dried reagent, was noted. Thus, in Table I below, no tube failed until the fifth run-through, when 1 tube failed. A set of tubes is considered a success if none of a set of 100 tubes failed on the first drop, and no more than 2 out of 100 failed on the second drop.

TABLE I

| # of Times Each Tube Dropped | Cumulative # of Failures out of 100 |
|---|---|
| 1 | 0 |
| 2 | 0 |
| 3 | 0 |
| 4 | 0 |
| 5 | 1 |

EXAMPLE 2

A set of 50 tubes was prepared and dropped as in Example 1, except that flange 18 was reduced in length so as to be only about 1.5 mm long. The results appear in Table IIA.

TABLE IIA

| # of Times Each Tube Dropped | Cumulative # of Failures out of 50 | # of Failures for 100* |
|---|---|---|
| 1 | 0 | 0 |
| 2 | 0 | 0 |
| 3 | 0 | 0 |
| 4 | 1 | 2 |
| 5 | 4 | 8 |

*Extrapolated from the column for 50.

For comparison purposes, a set of comparative examples was prepared by repeating Example 2, except that the flange 18 was cut off to leave only a suggestion of its presence—a length of less than about 0.5 mm. The results appear in Table IIB, and represent a failed set.

TABLE IIB

| | Comparative Example | |
|---|---|---|
| # of Times Each Tube Dropped | Cumulative # of Failures out of 50 | # of Failures for 100* |
| 1 | 0 | 0 |
| 2 | 6 | 12 |
| 3 | 9 | 18 |
| 4 | 10 | 20 |
| 5 | 10 | 20 |

*Extrapolated from the column for 50.

EXAMPLE 3

A set of 50 tubes was prepared and dropped as in Example 1, except that flange 18 was reduced in thickness to a value of only about 0.5 mm. The results appear in Table III.

TABLE III

| # of Times Each Tube Dropped | Cumulative # of Failures out of 50 | # of Failures for 100* |
|---|---|---|
| 1 | 0 | 0 |
| 2 | 1 | 2 |
| 3 | 2 | 4 |
| 4 | 6 | 12 |
| 5 | 9 | 18 |

*Extrapolated from column for 50.

Thus the flange 18 can be as thin as about 0.5 mm, and still provide adequate shock absorbance under this test.

EXAMPLE 4—REPEAT OF EXAMPLE 1

A set of 50 tubes was prepared and dropped identical to Example 1, but by a different experimenter, to see if the experiment was sensitive to the person doing the testing. The results appear in Table IV:

TABLE IV

| # of Times Each Tube Dropped | Cumulative # of Failures out of 50 | # of Failures for 100* |
|---|---|---|
| 1 | 0** | 0 |
| 2 | 1** | 2 |
| 3 | 3** | 6 |
| 4 | 8** | 16 |
| 5 | 13** | 26 |

*Extrapolated from column for 50.
**Substantially higher failure rates occur if the distance dropped is significantly larger than 68.2 cm, e.g., if it is at least 81.3 cm.

The results of Table IV are considered to be within experimental error of the results of Table I.

The invention has been described in detail with particular reference to certain preferred embodiments thereof, but it will be understood that variations and modifications can be effected within the spirit and scope of the invention.

What is claimed is:

1. In a container having a sidewall, a bottom wall joined to said sidewall at a junction point, and a reagent deposited on an inside surface of said bottom wall;

the improvement wherein said container further includes absorber means extending from said bottom wall at or below said junction point for absorbing shock, said absorber means having a length and thickness sufficient, when said container is dropped bottom wall first at a distance of 68.6 cm onto a hard surface with a container weight of 1.716 g, to prevent a dried reagent weighing 0.016 g deposited onto said inside surface from being dislodged, and wherein said container and said absorber means comprise a plastic that is sufficiently flexible as to allow said sidewall adjacent said bottom wall to be squeezed by finger pressure.

2. A container as defined in claim 1, wherein said side wall, said absorber means and said bottom wall are formed from polyethylene.

3. A container as defined in claim 1, wherein said absorber means comprises a flexible flange extending from said bottom wall approximately at the middle of said bottom wall.

4. A container as defined in claim 1, wherein said absorber means comprise a flexible skirt extending from a surface of said bottom wall.

5. A container as defined in claim 4, wherein said skirt extends around the entire circumference of said bottom wall.

6. A container as defined in claim 4, wherein portions of said skirt join together approximately at the middle of said bottom wall forming a shock-absorbing bubble.

* * * * *

UNITED STATES PATENT AND TRADEMARK OFFICE

CERTIFICATE OF CORRECTION

PATENT NO. : 4,968,486

DATED : November 06, 1990

INVENTOR(S) : Dennis R. Zander

It is certified that error appears in the above-identified patent and that said Letters Patent is hereby corrected as shown below:

Column 1, line 47 should read: cent the bottom wall being flexible,

Column 1, line 66 should read: upon reference to the following Description of the Pre- Column 2, line 66 should read: going types including nonisotopic tags such as enzymes, Column 3, line 3 should read: In further accord with the invention, the container Column 6, line 2 should read: cludes absorber means extending only from said bottom

Signed and Sealed this

Nineteenth Day of May, 1992

*Attest:*

DOUGLAS B. COMER

*Attesting Officer*

*Acting Commissioner of Patents and Trademarks*